United States Patent [19]

Yamada et al.

[11] Patent Number: 5,260,471
[45] Date of Patent: Nov. 9, 1993

[54] PROCESS FOR PRODUCING TRIALKOXYSILANE

[75] Inventors: Yoshinori Yamada; Katsuyoshi Harada, both of Nagoya, Japan

[73] Assignee: Toagosei Chemical Industry Co., Ltd., Tokyo, Japan

[21] Appl. No.: 3,469

[22] Filed: Jan. 12, 1993

[30] Foreign Application Priority Data

Jan. 13, 1992 [JP] Japan .................. 4-023141

[51] Int. Cl.$^5$ .......................... C07F 7/04; C07F 7/18
[52] U.S. Cl. ........................................ 556/470
[58] Field of Search .................................. 556/470

[56] References Cited

U.S. PATENT DOCUMENTS

| | | | |
|---|---|---|---|
| 3,072,700 | 1/1963 | de Wit | 260/448.8 |
| 4,931,578 | 6/1990 | Ohta et al. | 556/470 |
| 5,084,590 | 1/1992 | Ritscher et al. | 556/470 |
| 5,103,034 | 4/1992 | Cho et al. | 556/470 |
| 5,166,384 | 11/1992 | Bailey et al. | 556/470 |

OTHER PUBLICATIONS

J. Amer. Chem. Soc., vol. 70, p. 2170, 1945.

Primary Examiner—Paul F. Shaver
Attorney, Agent, or Firm—Sughrue, Mion, Zinn, Macpeak & Seas

[57] ABSTRACT

A process for producing a trialkoxysilane comprising reacting metallic silicon and an alkyl alcohol having from 1 to 4 carbon atoms in the presence of a catalyst, in which the reaction is carried out in a gaseous phase in the presence of a halide. The process achieves a high selectivity of a trialkoxysilane and a high conversion of silicon while inhibiting formation of by-products. Where the process of the present invention is carried out in a fluidized bed system, a satisfactory fluid state can be maintained, and the reaction temperature can easily be controlled.

17 Claims, No Drawings

5,260,471

PROCESS FOR PRODUCING TRIALKOXYSILANE

FIELD OF THE INVENTION

This invention relates to an efficient process for producing a trialkoxysilane which is useful as a starting material of silane coupling agents, etc.

BACKGROUND OF THE INVENTION

Alkoxysilanes are useful as starting materials for various silane coupling agents, insulating thin films, etc In particular, trialkoxysilanes are in large demand as having an SiH bond in the molecule thereof and being chemically more stable than monoalkoxysilanes or dialkoxysilanes, and it has been demanded to develop a process for producing them at high efficiency and low cost.

Known processes for producing a trialkoxysilane include a process comprising reacting a chlorosilane with a lower alkyl alcohol. However, besides being expensive, the chlorosilane by-produces hydrochloric acid, which not only makes purification of the product difficult but causes corrosion of the reaction apparatus.

A process comprising directly reacting metallic silicon and an alkyl alcohol is also known. This reaction is carried out in a vapor phase of a liquid phase in the presence of a catalyst, e.g., a copper catalyst, as described in U.S. Pat. Nos. 3,072,700 and 4,931,578. Where the reaction is effected in a liquid phase, the reaction rate and the silicon conversion per unit reactor volume are lower and the cost is higher, due to use of reaction solvents having a high boiling point, than in the reaction in a vapor phase. In addition, since the reaction residue contains high-boiling products, etc. and is therefore sludgy, it is difficult to treat. Further, the reaction solvent may be incorporated into the reaction product, making purification of the product complicated. In order to increase selectivity of the trialkoxysilane, it is known to add a halide to the liquid reaction system, as described in U.S. Pat. No. 4,931,578. However, the halide added is dissolved in a solvent used in large quantities so that it must be used in large quantities. As a result, the halide and the solvent react with each other to produce a by-product, which makes the solvent non-reusable.

A vapor phase process for efficiently producing a trialkoxysilane has thus been desired. A conventionally known vapor phase process as described in J. Amer. Chem. Soc., Vol. 70, p. 2170 (1945) preferentially produces a tetraalkoxysilane, a higher order compound, resulting in a low selectivity of the desired trialkoxysilane. Besides, the process achieves a low silicon conversion.

In addition, the inventors have found in the course of their study that the conventional vapor phase process involves the following problem when carried out on an industrial scale by using a fixed-bed reactor. Because the direct reaction between metallic silicon and an alkyl alcohol is a solid-gas reaction accompanied by great heat generation, it is influenced by cooling conditions when effected on an increased scale. In some cases, it is necessary to drop the feed rate of the alcohol in order to control the reaction, resulting in a reduction in reaction rate. Further, a temperature distribution occurs in the reactor, making it difficult to control the temperature uniformly. As a result, a tetraalkoxysilane and a dialkoxysilane are by-produced besides the desired trialkoxysilane, resulting in a substantial reduction in yield of the trialkoxysilane.

Where a fluidized bed reactor is used for uniform reaction in the reactor and for easy control of the reaction temperature, and the reaction is carried out at a lower temperature in order to increase the selectivity of a trialkoxysilane, there would arise various problems, such as a cessation of the fluid state, a reduction in conversion of metallic silicon, an increase of by-products, and the like, consequently failing to increase the selectivity as expected.

SUMMARY OF THE INVENTION

Accordingly, an object of the present invention is to provide a process for producing a trialkoxysilane which achieves a high selectivity of a trialkoxysilane and a high conversion of metallic silicon while suppressing formation of by-products and thereby causing no problem in the treatment of the reaction residue or the purification of the product.

Another object of the present invention is to provide a process for producing a trialkoxysilane on an industrial scale which, when carried out by using a fluidized bed reactor for easy control of the reaction temperature and by decreasing the reaction temperature for an increased selectivity, maintains the fluid state and inhibits formation of by-products.

The present invention provides a process for producing a trialkoxysilane comprising reacting metallic silicon and an alkyl alcohol having from 1 to 4 carbon atoms in the presence of a catalyst, in which the reaction is carried out in the presence of a halide in a vapor phase, preferably in a fluidized bed system.

DETAILED DESCRIPTION OF THE INVENTION

Metallic silicon which can be used as a reactant in the present invention suitably has a purity of at least 80% by weight and has a particulate shape. While not limiting, the average particle size of the metallic silicon is preferably not more than 2 mm, more preferably from 25 to 500 $\mu$m, and most preferably from 50 to 300 $\mu$m.

The alkyl alcohol, the other reactant, may have either a straight chain structure or a branched structure and includes methanol, ethanol, n-propanol, iso-propanol, n-butanol, sec-butanol, iso-butanol, and t-butanol, with methanol and ethanol being preferred. The effects of the present invention in improving the selectivity of a trialkoxysilane and the conversion of silicon are particularly pronounced in a process for producing triethoxysilane starting with ethanol as obviously revealed in Examples in view of Comparative Examples hereinafter described.

The alkyl alcohol preferably has a purity of at least 95% by wight. In particular, an alkyl alcohol whose water content has been decreased to 2000 ppm or less, and especially 500 ppm or less, by using a desiccant, etc. is preferred.

The feed rate of an alkyl alcohol to the reaction system preferably ranges from 10 to 1000 mmol/hr, and more preferably from 50 to 500 mmol/hr, per mol of metallic silicon. If it exceeds 1000 mmol/hr, the unreacted alkyl alcohol increases, which is not economical. If the alkyl alcohol feed rate is too low, the yield of a trialkoxysilane is reduced.

The alkyl alcohol may be fed either alone or as diluted with other gases.

The trialkoxysilane which can be obtained in the present invention has an alkoxy group derived from the starting alkyl alcohol and includes trimethoxysilane, triethoxysilane, tri-n-propoxysilane, triisopropoxysilane, tri-n-butoxysilane, tri-sec-butoxysilane, triisobutoxysilane, and tri-t-butoxysilane.

The catalyst which can be used in the present invention includes copper catalysts, zinc catalysts, and nickel catalysts. While not limiting, copper catalysts are preferred. Specific examples of suitable copper catalysts are inorganic copper compounds, such as copper salts (e.g., cuprous chloride, cupric chloride, copper bromide, copper iodide, copper fluoride, copper carbonate, copper sulfate, copper acetate, copper oxalate, and copper thiocyanate), copper hydroxide, copper cyanide, copper sulfide, and copper oxide; organocopper compounds, such as methyl copper and ethyl copper; and metallic copper, with cuprous chloride being particularly preferred.

The catalyst may be supplied to the reaction system in the form of a mixed powder with metallic silicon or as supported on metallic silicon. If desired, the catalyst may be subjected to an activation treatment, such as a heat treatment.

The catalyst is usually used in an amount of from 0.5 to 50% by weight, and preferably from 5 to 30% by weight, based on metallic silicon.

The halide which can be used in the present invention includes organic or inorganic compounds having a halogen atom in the molecule and capable of maintaining a gaseous state in the reaction system. Suitable organic halide compounds include a fluoride, a chloride, a bromide, etc. of a straight-chain or branched lower alkane, such as halogenated hydrocarbons containing 1 or 2 carbon atoms, e.g., methyl chloride, ethyl chloride, trichloroethylene, and 1,1,1-trichloroethane, with methyl chloride an ethyl chloride being preferred. Examples of usable inorganic halide compounds are halogen hydrides, e.g., hydrogen fluoride, hydrogen chloride, hydrogen bromide, and hydrogen iodide; halogen molecules, e.g., fluorine, chlorine, bromine, and iodine; and other inorganic halogen compounds.

The halide is supplied to the reaction system in its gaseous form accompanied, in most cases, by other gases. It may be supplied together with the alkyl alcohol.

The feed rate of the halide to the reaction system preferably ranges from 0.01 to 10 mmol, and more preferably from 0.1 to 1 mmol, per mol of the alkyl alcohol. Too a high feed rate only results in an increased cost. If the feed rate is less than 0.01 mmol, sufficient improvement in selectivity of a trialkoxysilane cannot be obtained.

The reaction according to the present invention is carried out in a vapor phase in which a gaseous alkyl alcohol and a gaseous halide are brought into contact with metallic silicon and a catalyst.

The reaction may be conducted either batchwise (i.e., metallic silicon and a catalyst are charged all at once at the beginning) or continuously (i.e., they are continuously fed to the reaction system).

It is also possible to conduct the reaction in various manners: for example, vibrations are given to metallic silicon and a catalyst; the reaction system is fluidized by means of a reactive gas (fluidized bed); metallic silicon and a catalyst is moved by vibration or a physical force (moving bed); or metallic silicon and a catalyst are fixed (fixed bed). The fluidized bed is especially recommended for its advantages in increasing the selectivity of a trialkoxysilane and the conversion of metallic silicon, inhibiting by-production, in handling the reaction residue, and in purifying the reaction product.

Any of the above-mentioned manners being applied, the alkyl alcohol and halide are fed to the reaction system in their vapor phase usually in a continuous manner or, if desired, intermittently.

The reactor to be employed is not limited in its design whether for the fixed bed or fluidized bed. The reactor may consist of a quartz pipe, a glass pipe, a metal pipe, etc. While not limiting, the reactor is preferably equipped with inlets for an alkyl alcohol, a halide or a fluidizing gas, a distributing plate, a heating and cooling means, an outlet for a reaction product, a pipe for withdrawal of a reaction residue, and a means for facilitating heat conduction, e.g., a fin or a coil, and has an airtight structure. Plates may be provided in the inside of the reactor, or the inside of the reactor may be partitioned into several zones.

Metallic silicon and a catalyst may be fed to the reaction system either in a batchwise manner or in a continuous manner.

The reaction according to the fluidized bed is carried out in a usual manner in which metallic silicon and a catalyst both in the form of a powder or a particle are fluidized by a fluidizing gas comprising a gaseous alkyl alcohol and a gaseous halide thereby effecting a solid-gas contact reaction. If desired, the fluidizing gas may contain an inert gas as a diluent.

The inert gas is incorporated into the fluidizing gas for the purpose of controlling the fluid state in the reactor. Any gas inert to a trialkoxysilane, such as nitrogen, argon, and hydrogen, may be used.

The linear velocity of the fluidizing gas is selected so as to fluidize the powdered or particulate substance, usually ranging from 10 to 1000 cm/min, preferably from 30 to 500 cm/min, and more preferably from 30 to 300 cm/min.

Other fluidization conditions are selected appropriately depending on the particle size of metallic silicon, the area of the reaction column, the reaction temperature, and so on. For example, reference may be made to Funtai Kogakukai (ed.), *Funtai Kocaku Binran*, p. 678 et seq. (1987).

The reaction is preferably carried out at a temperature ranging from 100 to 450° C., and particularly from 100 to 350° C. At temperatures lower than 100° C., a reduction in the conversion of metallic silicon results. At temperatures exceeding 450° C., the alkyl alcohol decomposes on contact with metallic silicon or the catalyst, leading to deactivation of the catalyst. From the standpoint of obtaining a very high conversion of metallic silicon, a temperature range of from 150 to 300° C. is the most preferred.

The reaction mixture obtained consists of a highly concentrated trialkoxysilane, the reusable unreacted alcohol, and trace amounts of by-products, such as mono- and dialkoxysilanes which can be reused as a starting material for a trialkoxysilane, and a tetraalkoxysilane which is unsuitable as a starting material for a trialkoxysilane. The desired trialkoxysilane can easily be recovered therefrom by known means, such as distillation.

As the reaction proceeds, metallic silicon and fine catalyst particles are also discharged together with the reaction product. They can easily be separated from a gaseous reaction product by means of a cyclone separator or from a liquefied reaction product by means of a centrifugal separator.

The reaction may proceed under either normal pressure or reduced pressure. Normal pressure is advantageous in that the apparatus used is not complicated and also from the economical consideration.

On the other hand, when the reaction is conducted under reduced pressure, high-boiling by-products, e.g., a tetraalkoxysilane (e.g., tetraethoxysilane) and a dimer or a trimer of silicon, can be driven out of the system smoothly, and the metallic silicon and the catalyst in the reactor can always be kept dry to prevent an uneven flow of the gas stream. In the case of a fluidized bed reaction, the reaction can be conducted in a homogeneous system in a stable manner for a long time to thereby further increase the silicon conversion or the alkoxysilane yield.

The "reduced pressure" as referred to above is suitably a pressure at which a tetraalkoxysilane and other high-boiling products are vaporized at the reaction temperature and specifically in a range of from 60 to 10 mmHg, and preferably from 460 to 660 mmHg. If the pressure exceeds 710 mmHg, distillation of the high-boiling products out of the reaction system cannot be effected smoothly, which causes a reduction in selectivity of a trialkoxysilane. If it is less than 60 mmHg, the alkyl alcohol would become thin and scare, which causes a reduction in yield of a trialkoxysilane.

The present invention is now illustrated in greater detail with reference to Examples, but it should be understood that the present invention is not deemed to be limited thereto. All the percents are by weight unless otherwise indicated.

EXAMPLE 1

In a porcelain pot mill were charged 300 g (10.68 mol) of metallic silicon having a chemical purity of 98% and an average particle size of 100 ⅔m and 15 g of cuprous chloride and ground for 8 hours. The mixed powder was packed in a quartz pipe (inner diameter: 30 mm; length: 600 mm) equipped with a pipe for introducing each of an alkyl alcohol and a halide having been vaporized in a vaporizer and, at the outlet thereof, a set of a cooler and a receiver for receiving the reaction mixture. The exhaust gas was discharged into the open air through a scrubbing bottle filled with liquid paraffin so as to prevent a back-flow of the air. The reactor was heated at 350° C. for 5 hours to activate the catalyst while feeding nitrogen gas at a rate of 30 ml/min.

The nitrogen feed was stopped, and the reactor was maintained at 250° C. Methanol vapor and methyl chloride vapor were then fed at a rate of 50 g/hr (1.56 mol/hr) and 3.5 ml/hr (0.1 mmol/hr), respectively, while feeding 20 ml/min of nitrogen gas in order to prevent a back-flow. One or two minutes from the commencement of the reaction, a reaction mixture began to be condensed from the cooler.

The change of the composition of the reaction mixture with time was analyzed by gas chromatography, and the time at which the composition comprised 100% alcohol was taken as a reaction end point. The reaction came to an end after 16 hours from the commencement to recover a reaction mixture containing a desired trialkoxysilane, i.e., trimethoxysilane in this case. The composition of the whole reaction mixture was analyzed, and the selectivity of a trialkoxysilane and the conversion of silicon were calculated according to the following equations. The results obtained are shown in Table 1 below.

$$\text{Trialkoxysilane Selectivity (\%)} = \frac{TRI}{TRI + TET} \times 100$$

(wherein TRI is the weight of trialkoxysilane, and TET is the weight of tetraalkoxysilane)

$$\text{Silicon Conversion (\%)} = 100 - \frac{MSR \times 100}{MSC}$$

(wherein MSR is the weight of metallic silicon in the reaction residue, and MSC is the weight of metallic silicon charged)

EXAMPLE 2

The same procedure as in Example 1 was repeated, except that the exhaust gas was introduced into an aspirator via a pressure reducing valve so that the inner pressure might be reduced to a desired degree and that the reaction was conducted at 180° C. under a pressure of 660 mmHg (adjusted by the aspirator).

The reaction completed in 21 hours from the commencement to recover a reaction mixture containing trimethoxysilane. The results of the analysis of the reaction mixture are shown in Table 1.

COMPARATIVE EXAMPLE 1

The same procedure as in Example 1 was repeated, except that methyl chloride was not introduced. The reaction completed in 16 hours. The results of the analysis are shown

COMPARATIVE EXAMPLE 2

The same procedure as in Example 2 was repeated, except that methyl chloride was not introduced. The reaction completed in 19 hours. The results of the analysis are shown in Table 1.

EXAMPLE 3

The same procedure as in Example 1 was repeated, except that methanol was replaced with 50 g/hr (1.09 mol/hr) of ethanol vapor and that ethyl chloride was fed at a rate of hr (0.1 mmol/hr) in place of methyl chloride. The reaction completed in 23 hours to obtain a reaction mixture containing triethoxysilane. The results of the analysis are shown in Table 1.

EXAMPLE 4

The same procedure as in Example 2 was repeated, except that methanol was replaced with 50 g/hr (1.09 mol/hr) of ethanol vapor and that ethyl chloride was fed at a rate of 24 ml/hr (0.1 mmol/hr) in place of methyl chloride. The reaction completed in 27 hours to obtain the reaction mixture containing triethoxysilane. The results of the analysis are shown in Table 1.

COMPARATIVE EXAMPLE 3

The same procedure as in Example 3 was repeated, except that ethyl chloride was not introduced. The reaction completed in 16 hours. The results of the analysis are shown

COMPARATIVE EXAMPLE 4

The same procedure as in Example 4 was repeated, except that ethyl chloride was not introduced. The reaction completed in 31 hours. The results of the analysis are shown in Table 1.

was observed. No sign of obstruction of the pipe for the produced gas was observed.

TABLE 1

| Example No. | Alkyl Alcohol | Reaction Conditions | | Composition of Reaction Mixture | | | | Trialkoxysilane Selectivity (%) | Silicon Conversion (%) |
| --- | --- | --- | --- | --- | --- | --- | --- | --- | --- |
| | | Reaction Pressure (mmHg) | Reaction Time (hr) | Tri- alkoxy- silane (wt %) | Tetra- alkoxy- silane (wt %) | Unreacted Alcohol (wt %) | Others* (wt %) | | |
| Example 1 | methanol | normal pressure | 16 | 79.2 | 19.3 | 0.5 | 1.0 | 80.4 | 70 |
| Example 2 | methanol | 660 | 21 | 92.7 | 1.0 | 1.9 | 4.4 | 98.9 | 96 |
| Compar. Example 1 | methanol | normal pressure | 16 | 46.4 | 49.5 | 3.1 | 1.0 | 48.4 | 65 |
| Compar. Example 2 | methanol | 660 | 19 | 79.2 | 14.9 | 1.0 | 4.9 | 84.2 | 90 |
| Example 3 | ethanol | normal pressure | 23 | 74.3 | 19.8 | 5.0 | 1.0 | 79.0 | 62 |
| Example 4 | ethanol | 660 | 27 | 82.4 | 4.8 | 9.7 | 3.2 | 94.5 | 80 |
| Compara. Example 3 | ethanol | normal pressure | 16 | 3.0 | 91.9 | 4.0 | 1.0 | 3.2 | 40 |
| Compara. Example 4 | ethanol | 660 | 31 | 58.3 | 9.7 | 29.1 | 2.9 | 85.7 | 70 |

Note:
*Mainly consist of a dialkoxysilane.

EXAMPLE 5

Fifty grams (1.78 mol) of metallic silicon (chemical purity: 98%; not through 100 mesh; average particle size: about 200 μ) and 5 g of cuprous chloride were ground in a ball mill for 8 hours. The mixed powder was heated at 450° C. for 5 hours in a nitrogen atmosphere to activate the catalyst.

The thus prepared catalyst-on-metallic silicon was charged in a vertical quartz column (inner diameter: 30 mm; height: 600 mm) equipped at the lower part thereof with an inlet pipe for introducing a diluting gas and a vaporized halide, a distributing plate, and an inlet pipe for introducing a vaporized alkyl alcohol and, at the outlet thereof, with a set of a cooler and a receiver for the reaction mixture. The exhaust gas was discharged into the open air through a scrubbing bottle filled with liquid paraffin so as to prevent a back-flow of the air.

Nitrogen gas as a diluting gas was introduced from the inlet at the lower part of the reactor at a rate of 500 ml/min, and the temperature was raised up to 180° C. while fluidizing the metallic silicon. Then, 10 ml/min (0.41 mmol/min) of ethyl chloride having been vaporized in a vaporizer was introduced from the inlet at the lower part of the reactor together with the above-mentioned nitrogen gas and, at the same time, separately vaporized ethanol was introduced at a rate of 20 g/hr (0.43 mol/hr) to conduct a reaction. After 1 or 2 minutes from the commencement of the reaction, a reaction mixture began to be condensed from the cooler.

The change of the composition of the reaction mixture with time was analyzed by gas chromatography, and the time at which the composition comprised 100% alcohol was taken as a reaction end point.

The reaction came to an end after 18 hours from the commencement to recover a reaction mixture containing a desired trialkoxysilane, i.e., triethoxysilane in this case. The composition of the whole reaction mixture, the selectivity of a trialkoxysilane, and the conversion of silicon are shown in Table 2 below.

The fluid state of the reaction system was satisfactory till the end of the reaction. The reaction residue consisting of metallic silicon which remained in the reactor after completion of the reaction was a fine powder and could easily be taken out of the reactor. No substantial adhesion of the residue to the inner wall of the reactor

EXAMPLE 6

The same procedure as in Example 5 was repeated, except that the reaction was carried out at 200° C. The reaction completed in 10 hours. The results of the analysis are shown in Table 2.

EXAMPLE 7

The same procedure as in Example 5 was repeated, except that the reaction was carried out at 200° C. and 10 g of cuprous chloride was used. The reaction completed in 10 hours. The results of the analysis are shown in Table 2.

EXAMPLE 8

The same procedure as in Example 5 was repeated, except that ethanol was replaced with methanol. The reaction completed in 8 hours to obtain a reaction mixture containing trimethoxysilane. The results of the analysis are shown in Table 2.

COMPARATIVE EXAMPLE 5

The same procedure as in Example 5 was repeated, except that ethyl chloride was not introduced.

The reaction system became hardly fluidized in several minutes from the commencement of the reaction and finally resulted in a substantial failure of fluidization after 1 hour. Consequently, it was difficult to keep the inner temperature uniform.

The reaction completed in 8 hours. Meanwhile the proportion of triethoxysilane in the withdrawn reaction mixture gradually decreased with time and, in turn, the proportion of tetraethoxysilane increased with time. The alkoxysilane content in the reaction mixture recovered at the end point consisted solely of tetraethoxysilane.

The results of the analysis are shown in Table 2.

The reaction residue comprising metallic silicon adhered to the inner wall of the reactor, needing washing

COMPARATIVE EXAMPLE 6

The same procedure as in Example 8 was repeated, except that ethyl chloride was not introduced. The reaction system became hardly fluidized in several minutes from the commencement of the reaction and finally resulted in a substantial failure of fluidization after 1 hour. The reaction completed in 6 hours. The results of the analysis are shown in Table 2.

TABLE 2

| Example No. | Alkyl Alcohol | Reaction Time (hr) | Composition of Reaction Mixture | | | | Trialkoxy-silane Selectivity (%) | Metallic Silicon Conversion (%) | Fluid State |
|---|---|---|---|---|---|---|---|---|---|
| | | | Tri-alkoxy-silane (wt %) | Tetra-alkoxy-silane (wt %) | Unreacted Alcohol (wt %) | Others* (wt %) | | | |
| Example 5 | ethanol | 18 | 51.7 | 0.0 | 48.3 | 0.0 | 100.0 | 67.9 | satisfactory |
| Example 6 | ethanol | 10 | 66.1 | 0.0 | 33.9 | 0.0 | 100.0 | 57.9 | satisfactory |
| Example 7 | ethanol | 10 | 96.0 | 0.0 | 4.0 | 0.0 | 100.0 | 78.3 | satisfactory |
| Example 8 | methanol | 8 | 84.3 | 0.0 | 15.7 | 0.0 | 100.0 | 76.4 | satisfactory |
| Compara. Example 5 | ethanol | 8 | 25.3 | 31.9 | 40.8 | 2.0 | 48.0 | 27.4 | hardly fluidized in a few minutes, almost 1 c fluidity in 1 hour |
| Compara. Example 6 | methanol | 6 | 30.2 | 34.3 | 32.2 | 3.3 | 46.8 | 38.6 | hardly fluidized in a few minutes, almost 1 c fluidity in 1 hour |

Note:
*Mainly consisted of a dialkoxysilane.

As described above, the present invention provides a process for producing a trialkoxysilane which achieves a high selectivity of a trialkoxysilane and a high conversion of silicon while inhibiting formation of by-products to eliminate difficulties or complicatedness in treating the residue or the reaction product. Where the process of the present invention is carried out in a fluidized bed system, a satisfactory fluid state can be maintained throughout the reaction, and the reaction temperature can easily be controlled.

While the invention has been described in detail and with reference to specific examples thereof, it will be apparent to one skilled in the art that various changes and modifications can be made therein without departing from the spirit and scope thereof.

What is claimed is:

1. A process for producing a trialkoxysilane comprising reacting metallic silicon and an alkyl alcohol having from 1 to 4 carbon atoms in the presence of a catalyst, in which the reaction is carried out in a vapor phase in the presence of a halide.

2. A process as claimed in claim 1, wherein the reaction is carried out in a fluidized bed system.

3. A process as claimed in claim 1, wherein the reaction is carried out at a temperature of from 100 to 450° C.

4. A process as claimed in claim 1, wherein the reaction is carried out under reduced pressure of from 60 to 710 mmHg.

5. A process as claimed in claim 1, wherein said catalyst is a copper catalyst.

6. A process as claimed in claim 1, wherein said catalyst is an inorganic copper compound, an organocopper compound, or metallic copper.

7. A process as claimed in claim 6, wherein said inorganic copper compound is a copper salt, copper hydroxide, copper cyanide, copper sulfide, or copper oxide.

8. A process as claimed in claim 7, wherein said copper salt is cuprous chloride, cupric chloride, copper bromide, copper iodide, copper fluoride, copper carbonate, copper sulfate, copper acetate, copper oxalate, or copper thiocyanate.

9. A process as claimed in claim 6, wherein said organocopper compound is methyl copper or ethyl copper.

10. A process as claimed in claim 1, wherein said alkyl alcohol is ethanol.

11. A process as claimed in claim 1, wherein said halide is an organic or inorganic halide compound in gaseous form at the reaction.

12. A process as claimed in claim 11, wherein said organic halide compound is a halide of straight-chain or branched lower alkane.

13. A process as claimed in claim 12, wherein said lower alkane is a halogenated hydrocarbon having one or two carbon atoms.

14. A process as claimed in claim 13, wherein said halogenated hydrocarbon is a chlorinated hydrocarbon.

15. A process as claimed in claim 14, wherein said chlorinated hydrocarbon is methyl chloride, ethyl chloride, trichloroethylene, or 1,1,1-trichloroethane.

16. A process as claimed in claim 14, wherein said chlorinated hydrocarbon is methyl chloride or ethyl chloride.

17. A process as claimed in claim 11, wherein said inorganic halide compound is a halogen hydride, or a halogen molecule.

* * * * *